United States Patent [19]

Scanlon

[11] Patent Number: 5,179,736
[45] Date of Patent: Jan. 19, 1993

[54] COMBINATION HEADSET AND FACE MASK DEVICE

[76] Inventor: Thomas A. Scanlon, 40 Hawthorne Ave., Barrington, R.I. 02806

[21] Appl. No.: 768,002

[22] Filed: Sep. 30, 1991

[51] Int. Cl.⁵ .............................. A61F 11/00
[52] U.S. Cl. .............................. 2/209; 2/6
[58] Field of Search .......... 2/6, 7, 9, 15, 206, 2/208, 209, 410, 421, 423, 424, DIG. 11

[56] References Cited

U.S. PATENT DOCUMENTS

| | | | |
|---|---|---|---|
| 2,782,423 | 2/1957 | Simon | 2/209 |
| 3,943,574 | 3/1976 | Yamaguchi | 2/209 |
| 4,756,028 | 7/1988 | Scanlon | 2/209 |
| 4,802,243 | 2/1989 | Griffiths | 2/6 |
| 5,046,192 | 9/1991 | Ryder | 2/6 |

Primary Examiner—Werner H. Schroeder
Assistant Examiner—Diana L. Biefeld
Attorney, Agent, or Firm—Robert J. Doherty

[57] ABSTRACT

Motion limiting means are provided on a combination headset and face mask device to eliminate the necessity of a rear head strap which is normally utilized to position the headband and to prevent its relative movement on the wearer's head when the face mask is adjusted as between upper and lower positions. This is accomplished by the provision of a bridge member which in essence pins the terminal band portion of the headband against its proximal ear cup thereby enabling the headband and ear cups to act as an unit and thus increase the frictional force available against the face mask moving the headband out of position.

12 Claims, 1 Drawing Sheet

000
COMBINATION HEADSET AND FACE MASK DEVICE

BACKGROUND AND OBJECTS OF THE INVENTION

This invention relates to a headset and face mask construction. It is common to mount protective face masks or shields from the sides of head encircling bands of headsets particularly sound reduction headsets in which a pair of ear cups are provided. Such face shields are commonly supported for relative rotational movement with respect to the headband between a lower use position and an upper storage position. Such relative face band movement very often causes the headband on which it is mounted to rotationally shift vis-a-vis the ear cups and to this end it is normal to provide a strap which connects to the headband and additionally is positioned about the rear of the wearer's head to give greater positioning stability to the main headband. This eleminates the actual and perceived need for the wearer to constantly readjust such after revising the face shield position. Such rear head straps however increase the complexity of such devices, and many wearers find them bothersome and simply eliminate them.

It is, accordingly, an object of the present invention to present a headset face shield combination device of the above generally-described type which includes means for better stabilizing the positional relationship between the headband and ear cups such that relative face shield movement between use positions will not displace the headband vis-a-vis the wearer's head.

A further object of the present invention is to provide an improved headset and face mask combination that eliminates the need for a rear headband and yet does so in an efficient and relatively simple manner.

These and other objects of the present invention are accomplished by temporarily or permanently fixing the spacial relationship of the ear cups and the headband ends to which they are attached to prevent substantial relative rotational movement between such elements and thus increase the stability by which the headband is positioned on the wearer's head which in turn reduces the likelihood rotational face shield movement supported thereby will undesirably alter such position.

Other objects, features and advantages of the invention shall become apparent as the description thereof proceeds when considered in connection with the accompanying illustrative drawing.

DESCRIPTION OF THE DRAWINGS

In the drawings which illustrate the best mode presently contemplated for carrying out the present invention.

DETAILED DESCRIPTION OF THE INVENTION

Figure 1:
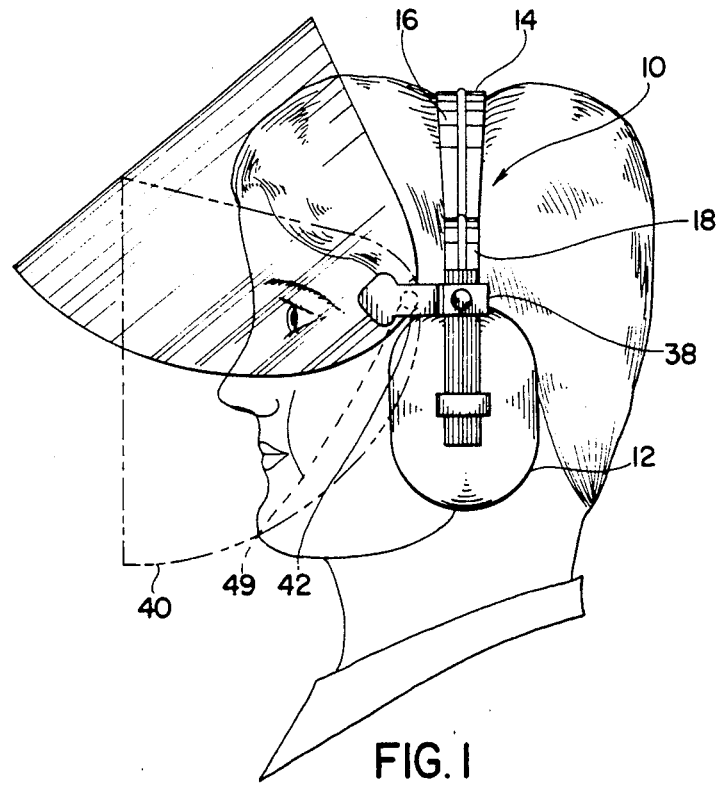
FIG. 1 is an elevational view showing the improved device of the present invention and positioned upon a wearer.

Turning now to the drawing and particularly FIG. 1 thereof, a headset 10 is shown positioned on the head of a wearer. Generally for the purpose of sound reduction, such headsets 10 include a pair of ear cups 12. Normally such ear cups 12 are positioned on terminal ends of headsets for at least partial rotational relationship thereto. In addition, the device of the present invention is provided with a protective face shield which is movable between upper and lower positions and is supported on the headset by a supporting finger in a manner which will hereinafter be more fully apparent.

The headset 10 more specifically includes a headband 14 having a first portion 16 which partially encircles the head and is supported thereon by a pair of side extensions 18 downwardly dependent therefrom. The side extensions 18 in turn terminate in lower outer and inner panels 20 and 22 respectively which in turn define an intermediate groove 24 therebetween. A slide 26 is positioned on the terminal end of extension 18 preferably between the outer and inner panels 20 and 22 respectively and is capable of sliding up and down with respect thereto to provide vertical adjustment of the ear cups 28. In this respect, it should be pointed out a connector member (not shown) extends inwardly from the slide 26 and projects into the ear cup 28 outer surface to provide normal rotational support thereof. The slide additionally includes opposed forward and rear side walls 30 disposed beneath and generally underlying and of the same lateral extent as opposed edges 32 of the outer panel 20. The exact manner in which such slide operates and its constructional details may be seen in greater detail by reference to applicant's U.S. Pat. No. 4,756,028 issued Jul. 12, 1988—the Specification of which is hereby specifically incorporated by specific reference thereto. It should also be pointed out that such exact slide and mounting configuration is not necessary for operation of the present device as will be hereinafter more fully obvious.

In addition to supporting the slide 26, the end extensions 18 further serve to mount a supporting finger 38 for the face shield 40. Such mounting finger 38 at its rear end in a connector 41 includes a body 42 having a pair of downwardly inwardly extending legs 44 which serve to partially encircle the outer panel and through which the body 42 may be vertically slidably positioned vis-a-vis the end extension 18. A set screw or other fastening means 46 extends through the body 42 and serves to fix the relative position of the finger 38 vis-a-vis the end extensions 18.

Forwardly extending from the body 42 is a front extension 48 by which the face shield 40 may be conventionally supported by means of the cooperation of an inwardly extending lug or pin 49 coacting with a recessed opening in the face shield. The face shield rotational movement may be limited by edge stops (not shown) coacting with an inwardly extending lug or pin mounted on the inner surface of the forward portion 48 or other conventional means. The important feature is that the face shield is supported either as above explained or by other means for relative movement between positions such as the lower use position shown by the dotted lines or the rest or storage position shown by the full lines in the FIG. 1 representation.

It is this relative motion of the face shield with respect to the headband 14 which causes in conventional devices a relative shifting of the headband either with respect to the wearer's head or with respect to the ear cups 28 or both. This relative motion is undesirable and is normally prevented by wearing a rear head strap which normally encircles a rear portion of the wearer's head and can be attached to the headband 14 via the set screws 46. The present invention eliminates the need for this rear head strap by introducing restraining means 60 to fix the relative rotational position of the end portions 18 vis-a-vis the ear cups 28. This is accomplished by a bridge member 62 having a pair of inwardly extending legs 64 terminating in ends 66 preferably rounded but which may be of any geometric configuration and are in turn adapted to fit into a pair of laterally-spaced openings 68 provided in the ear cups 28. Such openings extend into the outer shell of the ear cups 28 a finite distance such that the inner surface 69 of the connector portion or connecting body 70 of the bridge member 62 will preferably be slightly outwardly spaced from the outer surface of the outer panel 20. In addition, the bridging member 62 width is preferably such that the legs 64 inner surfaces are positioned proximal to or contact the opposed edges 32 of the outer shell 20 as well as the side walls 30 of the sliding member 26. In this manner then the bridging member 62 prevents the normal relative possible rotational movement between the ear cups 28 and the head band 14 terminal ends. Accordingly, this provides a more secure positioning of the headband 14 upon the wearer's head since, in effect, not only is the partial encircling portion 16 contacting the wearer's head but the ear cups 28 additionally contact the wearer's ears and head sides and both now become a unitary construction such that more bearing force vis-a-vis the wearer's head is brought about to support the position of the headband thereon. Accordingly, a greater force would be necessary to dislodge such positioning as by when the face shield 40 is moved from position to position.

Figure 2:
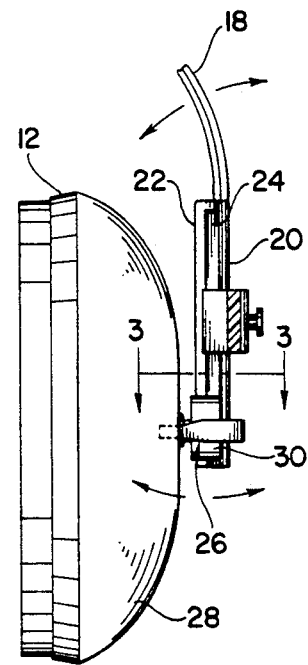
FIG. 2 is a side elevational view with of the ear cups and the means by which it is mounted to the circling headband.
Figures 3, 4:
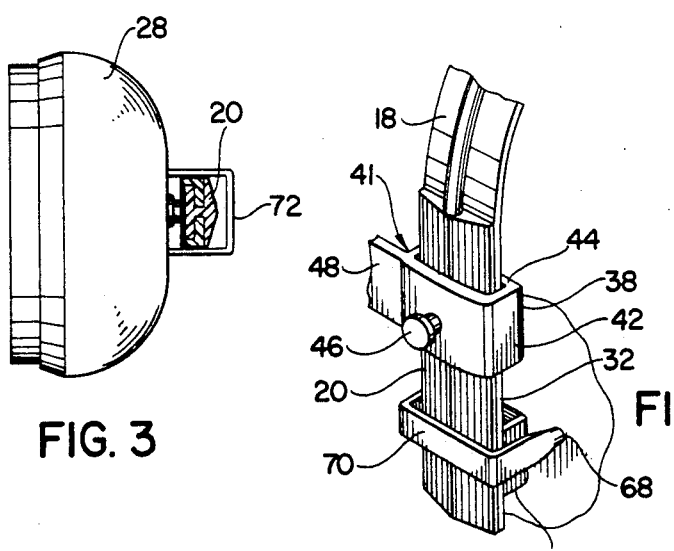
FIG. 3 is a partial sectional view taken along the line 3—3 of FIG. 2.
FIG. 4 is a partial perspective view of a terminal end band portion showing in particular the interrelationship between such and the ear cup supported thereby.
Figure 5:
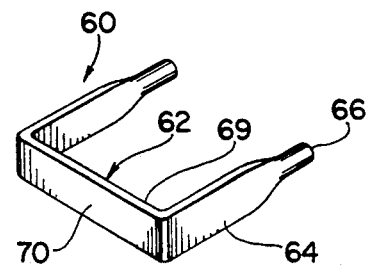
FIG. 5 is a perspective view of the restraining means forming a part of the present invention.

In addition to restraining such possible rotational movement present in prior art devices, the bridging member 62 of the present invention also preferably presents its connecting portion 70 in a position that is slightly outwardly spaced from the outer surface of the outer panel 20 so that some relative arcuate rocking of the headband 14 and its terminal portions in the direction of the arrows shown in FIG. 2 is permitted to accommodate better fit on different wearers. There may be cases, however, when it is not desirable to achieve such potential rocking action and in those cases the depth of the openings 68 in the ear cups 28 is dimensioned such that a snug contact between the inner surface of the bridging member 70 and the outer surface of the outer shell 20 is achieved.

While there is shown and described herein certain specific structure embodying this invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. An improved headset and face mask combination device wherein the headset is of the type having a flexible headband adapted to overlie the wearer's head and terminating in ends adapted for disposition opposite the wearer's ears and each such end in turn provided with an ear cup attached thereto and having generally rotational movement with respect to the end to which it is attached and at least some pivotal back and forth lateral movement in a plane defined by the transverse extent of said headband and a face mask rotationally movable between upper and lower positions supported from said headband; the improvement comprising, restraining means for essentially eliminating possible relative rotational motion of said ear cups relative to said headband terminal ends, said restraining means including a bridge member overlying portions of each said headband end, said bridge member further including means for fixedly attaching itself to said ear cups at two laterally-spaced locations on said ear cups and on either side of said headband ends.

2. The improved device of claim 1, said band ends including a vertically oriented end panel having an outer surface and an inner surface, said inner surface disposed face to face to said ear cup, said bridge member having a pair of inwardly extending legs having opposed outer and inner terminal ends connected by a connecting body at said outer ends, said ear cups having means for receiving said leg inner terminal ends so as to position said bridging member to overlie said end panel.

3. The improved device of claim 1, said band ends including a vertically oriented end panel having an outer surface and an inner surface, said inner surface disposed face to face to said ear cup, said bridge member having a pair of inwardly extending legs having opposed outer and inner terminal ends connected by a connecting body at said outer ends, said ear cups having openings for receipt of said leg inner terminal ends so as to position said bridging member to overlie said end panel.

4. The improved device of claim 3, said ear cup openings having means for limiting the inward positioning of said legs so as to outwardly space said bridging member from the outer surface of said end panel so as to permit pivotal rocking motion of said headband vis-a-vis said ear cups in a plane generally defined by said headband.

5. The improved device of claim 3, wherein said ear cups are attached to said band ends by a vertically adjustable slide member disposed between said band ends and said ear cups and in turn having a body with front and rear side walls, said bridge legs adapted to contact said front and rear side walls so as to restrain rotational movement.

6. The improved device of claim 5, said bridge member connecting body having an inner surface disposed towards said ear cup and wherein said inner surface of said connecting body contacts said end panel outer surface so as to additionally restrain rotational movement.

7. The improved device of claim 3, said bridge member connecting body having an inner surface disposed towards said ear cup and wherein said inner surface of said connecting body contacts said end panel outer surface.

8. An improved headset and face mask combination device wherein the headset is of the type having a flexible headband adapted to overlie the wearer's head and terminating in ends adapted for disposition opposite the wearer's ears and each such end in turn provided with an ear cup attached thereto and having generally rotational movement with respect to the end to which it is attached and at least some pivotal back and forth lateral movement in a plane defined by the transverse extent of said headband and a face mask rotationally movable between upper and lower positions supported from said headband; the improvement comprising, restraining means for essentially eliminating possible relative rotational motion of said ear cups relative to said headband terminal ends, said restraining means including a bridge member overlying and contacting portions of each said headband end, said bridge member further including means for fixedly attaching itself to said ear cups, said band ends including a vertically oriented end panel having an outer surface and an inner surface, said inner surface disposed face to face to said ear cup, said bridge member having a pair of inwardly extending legs having opposed outer and inner terminal ends connected by a connecting body at said outer ends, said ear cups having openings for receipt of said leg inner terminal ends so as to position said bridging member to contact said end panel.

9. The improved device of claim 8, said bridge member connecting body having an inner surface disposed towards said ear cup and wherein said inner surface of said connecting body contacts said end panel outer surface.

10. The improved device of claim 8, said ear cup openings having means for limiting the inward positioning of said legs so as to outwardly space said bridging member from the outer surface of said end panel so as to permit pivotal rocking motion of said headband vis-a-vis said ear cups in a plane generally defined by said headband.

11. The improved device of claim 8, wherein said ear cups are attached to said band ends by a vertically adjustable slide member disposed between said band ends and said ear cup and in turn having a body with front and rear side walls, said bridge legs adapted to contact said front and rear side walls so as to restrain rotational movement.

12. The improved device of claim 11, said bridge member connecting body having an inner surface disposed towards said ear cup and wherein said inner surface of said connecting body contacts said end panel outer surface so as to additionally restrain rotational movement.

* * * * *